United States Patent
Zhang et al.

(10) Patent No.: US 9,464,022 B2
(45) Date of Patent: Oct. 11, 2016

(54) METHOD OF TRANSFORMING BIOMASS INTO LACTIC ACID WITH MODIFIED BETA ZEOLITES

(71) Applicant: TONGJI UNIVERSITY, Shanghai (CN)

(72) Inventors: Yalei Zhang, Shanghai (CN); Zheng Shen, Shanghai (CN); Wenjie Dong, Shanghai (CN); Xuefei Zhou, Shanghai (CN)

(73) Assignee: TONGJI UNIVERSITY (CN)

( * ) Notice: Subject to any disclaimer, the term of this patent is extended or adjusted under 35 U.S.C. 154(b) by 0 days.

(21) Appl. No.: 14/928,755

(22) Filed: Oct. 30, 2015

(65) Prior Publication Data

US 2016/0046555 A1   Feb. 18, 2016

(30) Foreign Application Priority Data

Nov. 7, 2014   (CN) .......................... 2014 1 0620383

(51) Int. Cl.
   *C07C 51/43*   (2006.01)
   *C07C 51/00*   (2006.01)
   *B01J 29/00*   (2006.01)

(52) U.S. Cl.
   CPC ................ *C07C 51/00* (2013.01); *B01J 29/00* (2013.01)

(58) Field of Classification Search
   CPC ..................................................... C07C 51/04
   USPC ........................................... 562/580; 560/179
   See application file for complete search history.

(56) References Cited

U.S. PATENT DOCUMENTS

| 6,306,364 B1 | 10/2001 | Valencia et al. |
| 7,901,663 B2 * | 3/2011 | Lenglet ................. C10G 1/002 423/648.1 |
| 2010/0121096 A1 | 5/2010 | Taarning et al. |

FOREIGN PATENT DOCUMENTS

DK      2184270 T3    4/2013

OTHER PUBLICATIONS

West et al. Journal of Catalysis, 269 (2010) 122-130.*
Hammond et al. Angew. Chem. Int. Ed. 2012, 51, 11736-11739.*

* cited by examiner

*Primary Examiner* — Scarlett Goon
*Assistant Examiner* — Ana Z Muresan
(74) *Attorney, Agent, or Firm* — Hauptman Ham, LLP

(57) ABSTRACT

A method of transforming biomass into lactic acid using modified beta zeolites is disclosed. The one-step preparation process of preparing catalyst in the invention is mild, economical and convenient. The biomass used as precursor is economic and easy to get. Meanwhile, the reaction process doesn't need to be protected by noble gases with high pressure. The catalyst can be reused and the yield of lactic acid is high.

9 Claims, 2 Drawing Sheets

METHOD OF TRANSFORMING BIOMASS INTO LACTIC ACID WITH MODIFIED BETA ZEOLITES

RELATED APPLICATIONS

The present application claims priority from China Application Number 201410620383.2, filed Nov. 7, 2014, the disclosure of which is hereby incorporated by reference herein in its entirety.

FIELD OF THE INVENTION

The present invention relates to lactic acid, and, in particular, to a method of transforming biomass into lactic acid using modified beta zeolites.

BACKGROUND OF THE INVENTION

Lactic acid is widely used in food, pharmaceutical, chemical industries and other technical fields. In food industry, lactic acid can be used as acidulant, emulsifier and preservative because it is a nontoxic food additive. In pharmaceutical industry, lactic acid can be used to disinfect operating rooms and other places; lactates and lactic acid esters can be used as drugs; especially polylactide is biocompatible so it can be used to make artificial limb. The artificial limb is of high strength, and the probability of inflammation and infection is low when applied to human body. In chemical industry, lactic acid is an important platform chemical, because it can be transformed into other useful chemicals, such as acetaldehyde, propanediol, propanoic acid and pyruvic acid, etc. Additionally, lactic acid can be used as skin brightener, moisturizer, antimicrobial and stabilizer. During recent years, there has been a great demand for the biodegradable polylactide. There is a large gap in lactic acid production worldwide.

The traditional method for preparing lactic acid is based on the anaerobic fermentation of corns, rice, wheat, and so on. It is the main method of lactic acid production at present. The major disadvantages associated with this method are the complicated process, the long production time and the inevitable need of adding acid alkali and other substances during the process. Meanwhile, the same amount of calcium lactate is produced with the production of lactic acid, thus it is of low efficiency and not environmental friendly. Lactic acid can also be produced through chemical composition of precursors including lactonitrile, acrylonitrile and propanoic acid. However, the method of lactonitrile needs to use hydrogen cyanide which is highly toxic, while acrylic acid and propanoic acid are expensive, so they can't be used for large-scale industrial production.

During the recent years, researchers are trying to look for suitable catalysts to produce lactic acid from biomass which is naturally abundant. But there are still two main disadvantages. Firstly, the yield of lactic acid can be improved by adding alkali, which however requires the vessel to be resistant to alkali. Additionally, the addition of alkali makes the separation of lactic acid more difficult and it does damage to the environment inevitably. Secondly, the yield of lactic acid is low, which limits its application. For these reasons, researchers have turned to the research of the derivatives of lactic acid, such as methyl lactate, achieving high yields. Denmark patent (PA 200801556, PA 200900757) first reported a one-step method to prepare lactic acid through glucose, fructopyranose and sucrose, etc. by solid Lewis acidic catalysts. The highest yield is up to 30%, which aroused worldwide attention. However, the catalysts were synthesized according to the hydrothermal method reported by the US patent (U.S. Pat. No. 6,306,364) which is complicated and costs up to 20 days. Importantly, the yield of lactic acid is rather low from the perspective of practical application Additionally, toxic hydrofluoric acid is used as mineralizer. I Comparing with traditional hydrothermal method, solid ion-exchange method has the advantages of less time consuming, simple operation, so it is suitable for large scale production.

SUMMARY OF THE INVENTION

The invention provides a one-step preparation process of transforming biomass into lactic acid using modified beta zeolites. The preparation of catalyst is to remove the aluminum from the beta zeolites using nitric acid solution and then fix specific metal to the dealuminated beta zeolites by solid-state ion exchange. The catalytic reaction is carried out in a closed teflon vessel in a stainless steel autoclave charged with biomass, catalysts and deionized water. The autoclave is heated on a rotary oven. Lactic acid is obtained in solution by centrifugation and the solids can be activated and reused.

DETAILED DESCRIPTION OF THE INVENTION

Figure 1:
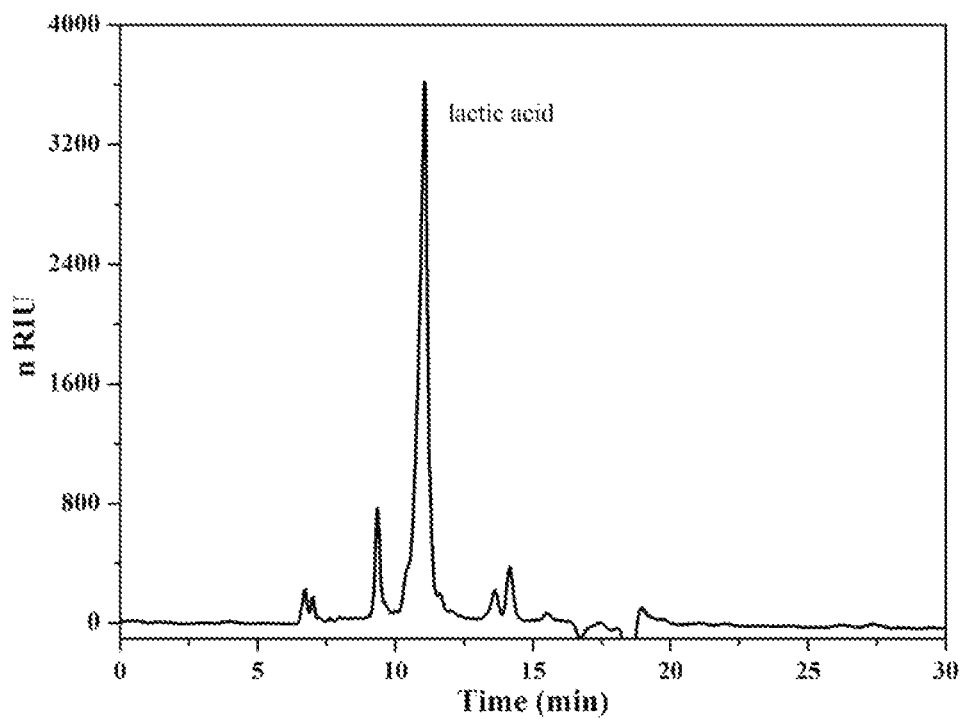
FIG. 1 is HPLC of the Catalytic Product over Zn—Sn-β zeolite of Example 9.

The purpose of the present invention is to provide a method of transforming biomass into lactic acid using modified beta zeolites. In particular, the invention is a process for the preparation of lactic acid compounds as main product from sucrose, lactose, glucose and fructopyranose in the presence of modified beta zeolites.

The present invention provides a method of transforming biomass into lactic acid using modified beta zeolites, comprising the following steps:

(1) The catalysts are prepared by solid ion-exchange method comprising: mixing beta zeolites with a concentrated nitric acid solution having a mass ratio, and stirring at 100° C. for 20 hrs to obtain a first mixture; then centrifuging and washing the first mixture for 7~9 times to obtain a centrifugation product, and drying the centrifugation product at 80° C. for 2 hrs and at 150° C. for 10 hrs to obtain dealuminated beta zeolites; then mixing the dealuminated beta zeolites with acetates to obtain a second mixture, and grinding; and finally calcining the ground second mixture to obtain a modified beta zeolite catalyst;

Wherein the mass ratio of beta zeolites to nitric acid solution is 1: (50~200); In the processing of mixing the dealuminated beta zeolites with acetates, for 1 g of dealuminated beta zeoiltes, the amount of acetates is 0.01~1.00 mmol (metal atom); and (2) catalytic reaction, comprising: adding biomass, modified beta zeolite catalysts and water with a mass ratio to an autoclave; then heating the autoclave in a rotary oven with a rotation rate for reaction to obtain reaction product, and then centrifuging the reaction product to obtain a liquid containing lactic acid and a solid containing the modified beta zeolite catalyst; and activating the solid for recycling the modified beta zeolite catalyst. Wherein the mass ratio of biomass to modified beta zeolite catalysts to water is 1: (0.01~1): (1~100), preferably 1:0.71:45.

In the above step (1), the acetates are selected from one or more of a group consisting of tin acetate, zinc acetate, cupric acetate, cerium acetate, chromium acetate and zirconium acetate.

In the above step (1), calcining the second mixture is performed in air atmosphere at 450~550° C. for 3~6 hrs.

In the above step (1), the mass ratio of beta zeolites to nitric acid solution is 1:110.

In the above step (2), the biomass comprises at least one selected from sucrose, lactose, glucose and fructopyranose.

In the above step (2), the rotation rate of rotary oven is 5~28 r/min.

In the above step (2), the autoclave is heated at 160~240° C. for 2~24 hrs.

In the above step (2), the centrifuging process is performed at a speed of 1000~15000 r/min for a centrifuging time of 1~20 min.

In the above step (2), the activation process comprises calcining the solid in air atmosphere at 450~550° C. for 6~10 hrs.

In this invention, solid ion-exchange method was used to prepare modified beta zeolites containing one metal or two metals including Zn, Sn, Cu, Ce, Cr or Zr. Lactic acid was produced from sugars by these catalysts in aqueous solution under auto-pressure and moderate temperature. Especially, Zn—Sn-Beta zeolite has both Lewis acidity and Lewis alkalinity characteristics. High yield of lactic acid is achieved by Zn—Sn-Beta zeolite in the absence of alkali, and the yield of lactic acid is up to 67.5%.

In the above step (2), there are acidoid, such as formic acid, levulinic acid and lactic acid, in the product of this catalytic reaction. In prior art, with the presence of such acidoid, the transformation of fructose to 5-hydroxymethylfurfural increased obviously, so the yield of lactic acid will be reduced. However, in this invention, the introduction of Zn to Sn-Beta zeolite allows the catalyst to have both Lewis acidity and Lewis alkalinity characteristics. Consequently, Zn—Sn-Beta zeolite can react with such acidoid in the product, thus leading to the decrease of adverse side-reaction, and obvious increase of lactic acid yield.

According to the invention, the following results can be obtained:

(1) In this invention, catalysts having good performance can be prepared conveniently within shorter preparation time, (2) In this invention, the biomass is used as precursor for preparing lactic acid. The biomass precursor is economic and easily available. Meanwhile, in the reaction process, there is no need for noble gases with high pressure for protection.

(3) In this invention, the catalyst can be recycled by centrifugation and calcination.

(4) In this invention, the yield of lactic acid is up to 67.5%.

EXAMPLES

The present invention will be further described below with reference to specific examples. However, these examples should not be construed to limiting the scope of the present invention.

Example 1-9 illustrate the preparation of catalysts using different kinds and amounts of acetates and the catalytic reaction under different conditions.

Example 1

Catalyst preparation: The beta zeolites are first mixed with a concentrated nitric acid solution with a mass ratio of 1:110 and stirred at 100° C. for 20 h. Then the mixture is centrifuged and washed for 8 times and dried at 80° C. for 2 h and 150° C. for 10 h to obtain dealuminated beta zeolites. 1 g of the dealuminated beta zeolites is mixed with 83.85 mg of cupric acetate (0.42 mmol Cu) and the mixture is grinded for 15 min and calcined in air at 550° C. for 6 h to obtain dealuminated Cu-beta zeolite catalyst.

Catalytic reaction: The catalytic reaction is carried out in a Teflon-lined stainless steel autoclave. The autoclave is charged with 225 mg of glucose, 160 mg of dealuminated Cu-beta zeolite catalyst, and 10 g of deionized water. The autoclave is placed in a rotary oven at 190° C. for 2 h with a rotate rate of 20 r/min. After centrifugation at 2000 r/min for 5 min, the remaining liquid is analyzed with High Performance Liquid Chromatography (HPLC). The yield of lactic acid turns out to be 16.4%.

Example 2

Catalyst preparation: The beta zeolites are first mixed with a concentrated nitric acid solution with a mass ratio of 1:110 and stirred at 100° C. for 20 h. Then the mixture is centrifuged and washed for 8 times and dried at 80° C. for 2 h and 150° C. for 10 h to obtain dealuminated beta zeolites. 1 g of the dealuminated beta zeolites is mixed with 92.19 mg of zinc acetate (0.42 mmol Zn) and the mixture is grinded for 20 min and calcined in air at 550° C. for 6 h to obtain dealuminated Zn-beta zeolite catalyst.

Catalytic reaction: The catalytic reaction is carried out in a Teflon-lined stainless steel autoclave. The autoclave is charged with 225 mg of sucrose, 160 mg of dealuminated Zn-beta zeolite catalyst, and 10 g of deionized water. The autoclave is placed in a rotary oven at 190° C. for 2 h with a rotate rate of 20 r/min. After centrifugation at 1000 r/min for 20 min, the remaining liquid is analyzed with HPLC. The yield of lactic acid turns out to be 25.5%.

Example 3

Catalyst preparation: The beta zeolites are first mixed with a concentrated nitric acid solution with a mass ratio of 1:110 and stirred at 100° C. for 20 h. Then the mixture is centrifuged and washed for 8 times and dried at 80° C. for 2 h and 150° C. for 10 h to obtain dealuminated beta zeolites. 1 g of the dealuminated beta zeolites is mixed with 99.46 mg of tin acetate (0.42 mmol Sn) and the mixture is grinded for 20 min and calcined in air at 550° C. for 6 h to obtain dealuminated Sn-beta zeolite catalyst.

Catalytic reaction: The catalytic reaction is carried out in a Teflon-lined stainless steel autoclave. The autoclave is charged with 225 mg of sucrose, 160 mg of dealuminated Sn-beta zeolite catalyst, and 10 g of deionized water. The autoclave is placed in a rotary oven at 190° C. for 2 h with a rotate rate of 20 r/min. After centrifugation at 2000 r/min for 5 min, the remaining liquid is analyzed with High HPLC. The yield of lactic acid turns out to be 26.7%.

Example 4

Catalyst preparation: The beta zeolites are first mixed with a concentrated nitric acid solution with a mass ratio of 1:110 and stirred at 100° C. for 20 h. Then the mixture is centrifuged and washed for 8 times and dried at 80° C. for 2 h and 150° C. for 10 h to obtain dealuminated beta zeolites. 1 g of the dealuminated beta zeolites is mixed with 96.24 mg of chromium acetate (0.42 mmol Cr) and the mixture is grinded for 20 min and calcined in air at 550° C. for 6 h to obtain dealuminated Cr-beta zeolite catalyst.

Catalytic reaction: The catalytic reaction is carried out in a Teflon-lined stainless steel autoclave. The autoclave is charged with 225 mg of glucose, 160 mg of dealuminated Cr-beta zeolite catalyst, and 10 g of deionized water. The autoclave is placed in a rotary oven at 190° C. for 2 h with a rotate rate of 20 r/min. After centrifugation at 5000 r/min for 2 min, the remaining liquid is analyzed with High HPLC. The yield of lactic acid turns out to be 34.5%.

Example 5

Catalyst preparation: The beta zeolites are first mixed with a concentrated nitric acid solution with a mass ratio of 1:110 and stirred at 100° C. for 20 h. Then the mixture is centrifuged and washed for 8 times and dried at 80° C. for 2 h and 150° C. for 10 h to obtain dealuminated beta zeolites. 1 g of the dealuminated beta zeolites is mixed with 99.46 mg of tin acetate (0.42 mmol Sn) and 83.85 mg of cupric acetate (0.42 mmol Cu) and the mixture is grinded for 30 min and calcined in air at 550° C. for 6 h to obtain dealuminated Cu—Sn-beta zeolite catalyst.

Catalytic reaction: The catalytic reaction is carried out in a Teflon-lined stainless steel autoclave. The autoclave is charged with 225 mg of sucrose, 160 mg of dealuminated Cu—Sn-beta zeolite catalyst, and 10 g of deionized water. The autoclave is placed in a rotary oven at 190° C. for 8 h with a rotate rate of 20 r/min. After centrifugation at 5000 r/min for 2 min, the remaining liquid is analyzed with High HPLC. The yield of lactic acid turns out to be 45.4.

Example 6

Catalyst preparation: The beta zeolites are first mixed with a concentrated nitric acid solution with a mass ratio of 1:110 and stirred at 100° C. for 20 h. Then the mixture is centrifuged and washed for 8 times and dried at 80° C. for 2 h and 150° C. for 10 h to obtain dealuminated beta zeolites. 1 g of the dealuminated beta zeolites is mixed with 198.92 mg of tin acetate (0.84 mmol Sn) and the mixture is grinded for 30 min and calcined in air at 550° C. for 6 h to obtain dealuminated Sn-beta zeolite catalyst.

Catalytic reaction: The catalytic reaction is carried out in a Teflon-lined stainless steel autoclave. The autoclave is charged with 225 mg of sucrose, 160 mg of dealuminated Sn-beta zeolite catalyst, and 10 g of deionized water. The autoclave is placed in a rotary oven at 190° C. for 8 h with a rotate rate of 20 r/min. After centrifugation at 2000 r/min for 5 min, the remaining liquid is analyzed with High HPLC. The yield of lactic acid turns out to be 50.1%.

Example 7

Catalyst preparation: The beta zeolites are first mixed with a concentrated nitric acid solution with a mass ratio of 1:110 and stirred at 100° C. for 20 h. Then the mixture is centrifuged and washed for 8 times and dried at 80° C. for 2 h and 150° C. for 10 h to obtain dealuminated beta zeolites. 1 g of the dealuminated beta zeolites is mixed with 76.98 mg of zirconium acetate (0.42 mmol Zr) and 133.24 mg of cerium acetate (0.42 mmol Ce) and the mixture is grinded for 30 min and calcined in air at 550° C. for 6 h to obtain dealuminated Zr—Ce-beta zeolite catalyst.

Catalytic reaction: The catalytic reaction is carried out in a Teflon-lined stainless steel autoclave. The autoclave is charged with 225 mg of glucose, 160 mg of dealuminated Zr—Ce-beta zeolite catalyst, and 10 g of deionized water. The autoclave is placed in a rotary oven at 190° C. for 8 h with a rotate rate of 20 r/min. After centrifugation at 5000 r/min for 2 min, the remaining liquid is analyzed with High HPLC. The yield of lactic acid turns out to be 48.6%.

Example 8

Catalyst preparation: The beta zeolites are first mixed with a concentrated nitric acid solution with a mass ratio of 1:110 and stirred at 100° C. for 20 h. Then the mixture is centrifuged and washed for 8 times and dried at 80° C. for 2 h and 150° C. for 10 h to obtain dealuminated beta zeolites. 1 g of the dealuminated beta zeolites is mixed with 99.46 mg of tin acetate (0.42 mmol Sn) and 92.19 mg of zinc acetate (0.42 mmol Zn) and the mixture is grinded for 20 min and calcined in air at 550° C. for 6 h to obtain dealuminated Zn—Sn-beta zeolite catalyst.

Catalytic reaction: The catalytic reaction is carried out in a Teflon-lined stainless steel autoclave. The autoclave is charged with 225 mg of glucose, 160 mg of dealuminated Zn—Sn-beta zeolite catalyst, and 10 g of deionized water. The autoclave is placed in a rotary oven at 190° C. for 8 h with a rotate rate of 20 r/min. After centrifugation at 5000 r/min for 2 min, the remaining liquid is analyzed with High HPLC. The yield of lactic acid turns out to be 65.2%.

Example 9

Catalyst preparation: The beta zeolites are first mixed with a concentrated nitric acid solution with a mass ratio of 1:110 and stirred at 100° C. for 20 h. Then the mixture is centrifuged and washed for 8 times and dried at 80° C. for 2 h and 150° C. for 10 h to obtain dealuminated beta zeolites. 1 g of the dealuminated beta zeolites is mixed with 99.46 mg of tin acetate (0.42 mmol Sn) and 92.19 mg of zinc acetate (0.42 mmol Zn) and the mixture is grinded for 30 min and calcined in flowing air at 550° C. for 6 h to obtain dealuminated Zn—Sn-beta zeolite catalyst.

Catalytic reaction: The catalytic reaction is carried out in a Teflon-lined stainless steel autoclave. The autoclave is charged with 225 mg of sucrose, 160 mg of dealuminated Zn—Sn-beta zeolite catalyst, and 10 g of deionized water. The autoclave is placed in a rotary oven at 190° C. for 8 h with a rotate rate of 20 r/min. After centrifugation at 5000 r/min for 2 min, the remaining liquid is analyzed with High Performance Liquid Chromatography (HPLC). The chromatogram is shown in FIG. 1. The yield of lactic acid turns out to be 67.5%.

Figure 2:
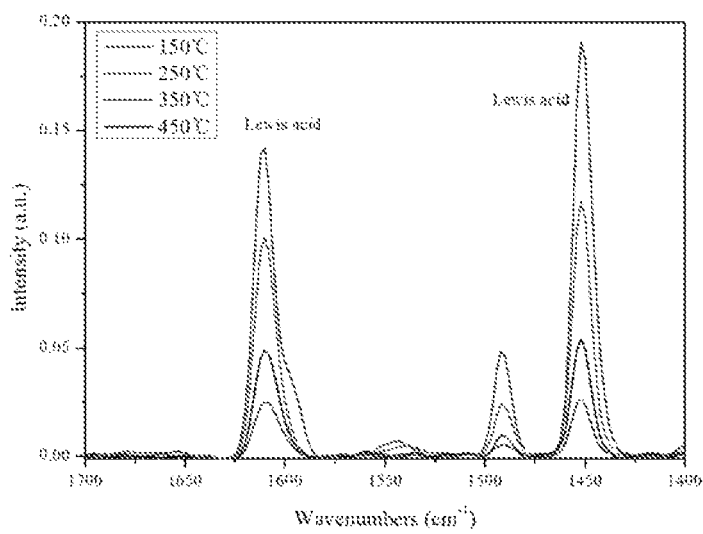
FIG. 2 is Lewis Acid Characterization of Zn—Sn-Beta of Example 9.

The Lewis Acid Characterization of this dealuminated Zn—Sn-Beta zeolite catalyst is shown in FIG. 2. As shown in FIG. 2, pyridine is used as a probe, the high relative intensity of the band at 1454 and 1622 $cm^{-1}$ represent Lewis acid sites.

Figure 3:
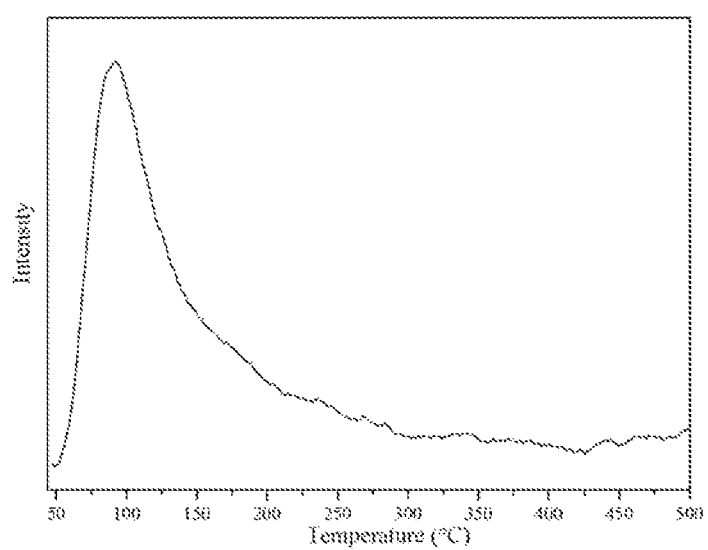
FIG. 3 is Lewis Alkali Characterization of Zn—Sn-Beta of Example 9.

The Lewis Alkali Characterization of dealuminated Zn—Sn-Beta zeolite catalyst is shown in FIG. 3. As shown in FIG. 3, Carbon dioxide is used as a probe, the high relative intensity of the band at 92° C. represents Lewis basic sites.

Example 10-12 illustrate the activation and reuse of catalysts.

Example 10

Catalyst activation: The solids obtained from the product of example 4 through centrifugation are calcined in air at 550° C. for 6 h to obtain 144 mg of solids.

Catalytic reaction: The catalytic reaction is carried out in a Teflon-lined stainless steel autoclave. The autoclave is charged with 200 mg of glucose, 144 mg of the zeolite catalyst after activation, and 10 g of deionized water. The autoclave is placed in a rotary oven at 190° C. for 8 h with a rotate rate of 20 r/min. After centrifugation at 5000 r/min for 2 min, the remaining liquid is analyzed with High HPLC. The yield of lactic acid turns out to be 37.8%.

Example 11

Catalyst activation: The solids obtained from the product of example 6 through centrifugation are calcined in flowing air at 550° C. for 6 h to obtain 148 mg of solids.

Catalytic reaction: The catalytic reaction is carried out in a Teflon-lined stainless steel autoclave. The autoclave is charged with 206 mg of glucose, 148 mg of the zeolite catalyst after activation, and 10 g of deionized water. The autoclave is placed in a rotary oven at 190° C. for 8 h with a rotate rate of 20 r/min. After centrifugation at 5000 r/min for 2 min, the remaining liquid is analyzed with High HPLC. The yield of lactic acid turns out to be 43.8%.

Example 12

Catalyst activation: The solids obtained from the product of example 9 through centrifugation are calcined in flowing air at 550° C. for 6 h to obtain 148 mg of solids.

Catalytic reaction: The catalytic reaction is carried out in a Teflon-lined stainless steel autoclave. The autoclave is charged with 206 mg of sucrose, 148 mg of the zeolite catalyst after activation, and 10 g of deionized water. The autoclave is placed in a rotary oven at 190° C. for 8 h with a rotate rate of 20 r/min. After centrifugation at 5000 r/min for 2 min, the remaining liquid is analyzed with High HPLC. The yield of lactic acid turns out to be 47.8%.

While the foregoing is directed to embodiments of the present invention, other and further embodiments of the invention may be devised without departing from the basic scope thereof, and the scope thereof is determined by the claims that follow.

The invention claimed is:

1. A method of transforming biomass into lactic acid using modified beta zeolites, comprising the following steps:
   (1) catalyst preparation, comprising:
      mixing beta zeolites with a concentrated nitric acid solution having a mass ratio, and stirring at 100° C. for 20 hrs to obtain a first mixture;
      then centrifuging and washing the first mixture for 7-9 times to obtain a centrifugation product, and drying the centrifugation product at 80° C. for 2 hrs and at 150° C. for 10 hrs to obtain dealuminated beta zeolites; and
      then mixing the dealuminated beta zeolites with acetates to obtain a second mixture, and grinding; and finally calcining ground second mixture to obtain the modified beta zeolite catalyst;
      wherein the mass ratio of beta zeolites to nitric acid solution is 1:(50-200);
      in which in the process of mixing the dealuminated beta zeolites with acetates, for 1 g of dealuminated beta zeolites, the amount of acetates is 0.01-1.00 mmol, and the amount of acetates is calculated based on the metal atom in the acetates;
      wherein the acetates are tin acetate and zinc acetate to yield a zinc-tin-beta zeolite catalyst; and
   (2) catalytic reaction, comprising:
      adding biomass, zinc-tin-beta zeolite catalyst prepared by step (1) and water with a mass ratio to an autoclave;
      then heating the autoclave in a rotary oven with a rotation rate for reaction to obtain a reaction product; and
      then centrifuging the reaction product to obtain a liquid which is lactic acid and a solid containing the zinc-tin-beta zeolite catalyst; and activating the solid for recycling the modified beta zeolite catalyst,
      wherein the mass ratio of biomass to zinc-tin-beta zeolite catalyst to water is 1:(0.01-1):(1-100).

2. The method according to claim 1, wherein in the step (1), calcining the second mixture is performed in flowing air atmosphere at 450-550° C. for 3-6 hrs.

3. The method according to claim 1, wherein in the step (1), the mass ratio of beta zeolites to nitric acid solution is 1:110.

4. The method according to claim 1, wherein in the step (2), the biomass comprises at least one selected from the group consisting of sucrose, lactose, glucose and fructopyranose.

5. The method according to claim 1, wherein in the step (2), the rotation rate of rotary oven is 5-28 r/min.

6. The method according to claim 1, wherein in the step (2), the autoclave is heated at 160-240° C. for 2-24 hrs.

7. The method according to claim 1, wherein in the step (2), the centrifuging process is performed at a speed of 1000-15000 r/min for 1-20 min.

8. The method according to claim 1, wherein in the step (2), the activation process comprises calcining the solid in flowing air atmosphere at 450-550° C. for 6-10 hrs.

9. The method of claim 1, wherein the mass ratio of biomass to zinc-tin-beta zeolite catalyst to water is 1:0.71:45.

* * * * *